(12) United States Patent
Cormier et al.

(10) Patent No.: US 8,288,727 B2
(45) Date of Patent: Oct. 16, 2012

(54) APPARATUS AND METHOD FOR RAPID AND ACCURATE QUANTIFICATION OF AN UNKNOWN, COMPLEX MIX

(75) Inventors: John Cormier, Edmonton (CA); Denis Dufour, Edmonton (CA)

(73) Assignee: Picomole Instruments Inc., Edmonton, Alberta (CA)

( * ) Notice: Subject to any disclaimer, the term of this patent is extended or adjusted under 35 U.S.C. 154(b) by 581 days.

(21) Appl. No.: 12/517,036

(22) PCT Filed: Dec. 18, 2007

(86) PCT No.: PCT/CA2007/002306
§ 371 (c)(1),
(2), (4) Date: Jul. 9, 2009

(87) PCT Pub. No.: WO2008/074142
PCT Pub. Date: Jun. 26, 2008

(65) Prior Publication Data
US 2010/0002234 A1    Jan. 7, 2010

Related U.S. Application Data

(60) Provisional application No. 60/875,374, filed on Dec. 18, 2006.

(51) Int. Cl.
*G01J 5/02* (2006.01)
*G01N 21/00* (2006.01)
*A61B 5/08* (2006.01)
(52) U.S. Cl. ............. 250/339.01; 356/436; 600/532
(58) Field of Classification Search .............. None
See application file for complete search history.

(56) References Cited

U.S. PATENT DOCUMENTS
7,101,340 B1 * 9/2006 Braun ................... 600/532
2004/0137637 A1   7/2004 Wang et al.

OTHER PUBLICATIONS

Kurochkin et al., "Three Mirror Cavity CO2 Lser for Intracavity Saturated-Absoprtion Spectroscopy." Optical Spectroscopy, vol. 65, No. 2, pp. 265-267, Aug. 1988.*

* cited by examiner

*Primary Examiner* — Gregory J Toatley
*Assistant Examiner* — Amanda Merlino
(74) *Attorney, Agent, or Firm* — Marsh Fischmann & Breyfogle LLP

(57) ABSTRACT

An apparatus and method for rapidly and accurately identifying and quantifying analytes in a complex mixture is disclosed. The apparatus comprises an ultra-sensitive cavity-enhanced spectrometer coupled to data-collection and analysis devices. The method comprises the use of a database containing the absorption cross-sections of various analytes to numerically determine the composition of the sample.

27 Claims, 4 Drawing Sheets

APPARATUS AND METHOD FOR RAPID AND ACCURATE QUANTIFICATION OF AN UNKNOWN, COMPLEX MIX

FIELD OF THE INVENTION

The invention relates to ultra-high-sensitivity absorption spectroscopy, in particular the simultaneous measurement of the concentration of multiple trace analytes using laser-based cavity-enhanced detection.

BACKGROUND OF THE INVENTION

All of the publications, patents and patent applications cited within this application are herein incorporated by reference in their entirety to the same extent as if the disclosure of each individual publication, patent application or patent was specifically and individually indicated to be incorporated by reference in its entirety.

Cavity ringdown spectroscopy (CRDS) is a technique that utilizes the resonance of light within an optical cavity to allow the measurement of very small concentrations of light-absorbing analytes. The optical cavity consists of two or more highly reflective mirrors, between which the sample containing the analytes to be measured is placed. Optical resonance is achieved by excitation of the cavity using light with appropriate frequency and mode characteristics, said light usually provided by a laser source. When the light used to excite resonance in the cavity is abruptly cut off, either by a modulation device or by the inherent pulse-like nature of the light beam, the light remaining in the cavity bounces between the cavity mirrors while its intensity decreases exponentially as function of time due to the attenuation by the cavity mirrors and the absorption by analytes within the cavity. This process is known as "cavity ringdown" (reference: "Development of an Infrared Cavity Ringdown Spectroscopy Experiment and Measurements of Water Vapor Continuum Absorption", John G. Cormier, PhD Thesis, 2002).

The rate of decay of light intensity within the cavity is usually determined by measuring the intensity of a small fraction of light exiting from one of the cavity mirrors as a pre-arranged leakage. The thousands of reflections that occur before the leakage signal intensity is too small to usefully measure create an effective beam path length several orders of magnitude longer than the separation between the mirrors. This effectively magnifies the attenuation of light by the analytes in the cavity, therefore very small concentrations of analytes can be measured.

Gas lasers have been used with photoacoustic cells for multi-component analyte detection, e.g. U.S. Pat. No. 6,363,772 by Berry where a CO overtone laser is used. Although photoacoustic techniques have been shown to be effective in the detection of trace gases (Photoacoustic Spectroscopy in Trace Gas Monitoring, Harren et. al., Encyclopedia of Analytical Chemistry, pp. 2203-2226, (J. Wiley & Sons 2000)), these techniques are not as effective in measuring absolute quantities of constituents as the cavity ring-down method. One of the reasons for this is that cavity ringdown measurements are purely ratiometric, that is they provide a means for direct measurement of light attenuation by absorbing molecules without requiring a priori knowledge of instrument parameters such as laser beam intensity, ringdown cavity length or mirror reflectivity. In contrast, photoacoustic spectroscopy is an indirect detection method where acoustic waves generated by heat fluctuations caused by the absorption of light by molecules in the sample are measured. Although potentially a very sensitive technique, photoacoustic spectroscopy suffers from several drawbacks that limit its ability to accurately measure analyte concentrations. Some of these noted in U.S. Pat. No. 5,528,040 by Lehmann:

(1) A quiet acoustic environment is required (therefore, use of an electric discharge or rapid flow of the sample leads to a substantial increase in noise);
(2) The sample is exposed to some average light flux, which can lead to photochemistry in some situations;
(3) The indirect nature of the detection makes determination of absolute absorption strengths difficult. The only practical way to calibrate the strength of the acoustic signal is to use a mixture of a gas which has some transition whose cross-section is already known along with the gas of interest. Even with such calibration, uncertainties on the order of 20% remain.

In order to measure analyte concentrations using infrared-range cavity-enhanced laser-based devices, the prior art teaches the tuning of a laser line to the frequency of a principal absorption line of the analyte of interest, and then measure the change in some physical parameter related to the absorption of light by the analyte at said frequency. For the case of cavity ringdown measurements, the measured physical parameter is the decay time of laser light intensity in the cavity, usually determined by proxy through measurement of a small amount of light designed to leak from one of the cavity mirrors. For photoacoustic spectroscopy, the measured quantity is the change in acoustic energy due to changes in heat resulting from the absorption of light by the analyte. A reference measurement is usually also made by tuning the laser frequency away from the absorption peak. The difference between the two measurements is then used to infer the amount of gas in the cell. Such a two-frequency method is described for example in Pat. WO02/090935 by Patel, where it is used to determine the concentrations of various gaseous compounds using laser-based photoacoustic cell measurements. The disadvantages of this method are that only one analyte at a time can be measured, low gas mixture pressures are usually required, and large measurement errors can occur due to the presence of unknown analytes in the mixture.

Situations exist where it is desired to measure the composition of a complex mixture of analytes to better than part-per-billion accuracy, under ambient atmospheric temperature and pressure conditions, without prior compositional knowledge or bias. Examples of said applications include, but are not limited to, human exhaled breath measurement for the diagnosis and monitoring of medical conditions, environmental monitoring of toxins, explosives detection and industrial process monitoring. Therefore there is a need to have an apparatus that can identify and quantify multiple analytes within an unknown, complex mixture in an accurate and unbiased manner, to a very high degree of sensitivity, without the added complexity of having to pre-concentrate the analytes or modify the pressure of the mixture.

SUMMARY OF THE INVENTION

The present art has suffered from an inability to accurately identify the presence of minute quantities of compounds in a gas or liquid at atmospheric pressures. Current laser-based, cavity-enhanced apparatus are designed to measure concentrations of one or more target analytes using source frequencies specially tuned to absorption lines of said analytes. The measurement methods they employ usually require low sample pressures, thereby introducing complexity to the sample delivery mechanism. These methods are biased towards targeted analytes and are susceptible to measurement errors due to the presence of unknown analytes in the cavity.

In addition, photoacoustic cavity-based methods tend to be inherently less accurate than cavity ringdown apparatus due to the indirect nature of the measurement of light absorption by the analytes.

The present invention provides for an apparatus comprising a source capable of emitting pulsed light at a plurality of widely-spaced monochromatic frequencies, a cavity-enhanced measurement chamber, a detector measuring a physical parameter related to the amount of light attenuation resulting from at least one analyte present in the measurement chamber, at least one device capable of collecting data from the detector, and at least one device in communication with the detector capable of comparing the absorption of each at least one analyte to a database of known analyte absorption cross-sections; wherein the measurement is performed at a plurality of well-defined light frequencies.

In one embodiment of the present invention, the source capable of emitting pulsed light at a plurality of widely-spaced monochromatic frequencies is able to emit at least two monochromatic frequencies simultaneously. In an alternative embodiment of the present invention, the source capable of emitting pulsed light at a plurality of widely-spaced monochromatic frequencies is capable of emitting multiple monochromatic frequencies sequentially.

In one embodiment of the present invention, the widely-spaced monochromatic frequencies are either known or determinable.

In a preferred embodiment of the present invention the cavity enhanced measurement chamber is a ringdown cavity.

In a preferred embodiment of the present invention, there is a mechanism for collecting a sample to be analyzed, in fluid communication with the measurement chamber, capable of delivering the sample to be analysed to the measurement chamber, and removing it from the measurement chamber and apparatus after a completed measurement.

In a preferred embodiment the method and apparatus of the present invention is used to analyze samples from an animal, including a human. In an even more preferred embodiment, the samples analyzed from an animal include breath.

The present invention also provides for a method of analysis of the electromagnetic absorption spectrum of a complex sample u comprising the assessment of absorption at N discrete frequencies, comprising A) Defining of M analytes for use with an initial model;
B) Defining an initial model, $Q_0$, consisting of M analytes and their concentrations $n_j$, where j=1 to M;
C) Estimating the concentrations $n_j$ of each analyte in the $Q_0$ model calculated from the absorbance measurement vector $y_i$, where i=1 to N is the electromagnetic frequency index, the matrix K whose elements $k_{ij}$ are the absorbances by the analytes j at each electromagnetic frequency i, and the measurement error covariance matrix $S_e$, using a technique such as, but not limited to, direct inverse least-squares estimation $$n = (K^T S_e^{-1} K)^{-1} K^T S_e^{-1} y$$

D) Performing the Systematic addition or removal of at least one light-absorbing analyte from the model $Q_0$ by cycling through a database of P known analytes, creating P new models $Q_1$ to $Q_p$
E) Comparing the fit of model $Q_0$ to the measurement vector y to the fit of models $Q_1$ through $Q_p$ to y, where the best-fit concentrations are obtained for each model using the method described in step C;
F) If the goodness-of-fit of the best-fitting of the $Q_1$ through $Q_p$ models compared to y is better than $Q_0$ to y, then the best-fitting of the $Q_p$ models is defined as $Q_0$;
G) Steps D through F are repeated until no further improvements to the goodness-of-fit of the model to the measurement vector y can be achieved by adding or removing analytes to the model. The goodness-of-fit may be estimated by calculating a fit parameter that incorporates the degrees of freedom (entropy) of the model, such as the Akaike Information Criterion.

The accompanying description illustrates preferred embodiments of the present invention and serves to explain the principles of the present invention

DETAILED DESCRIPTION OF THE PRESENT INVENTION

Figure 1:
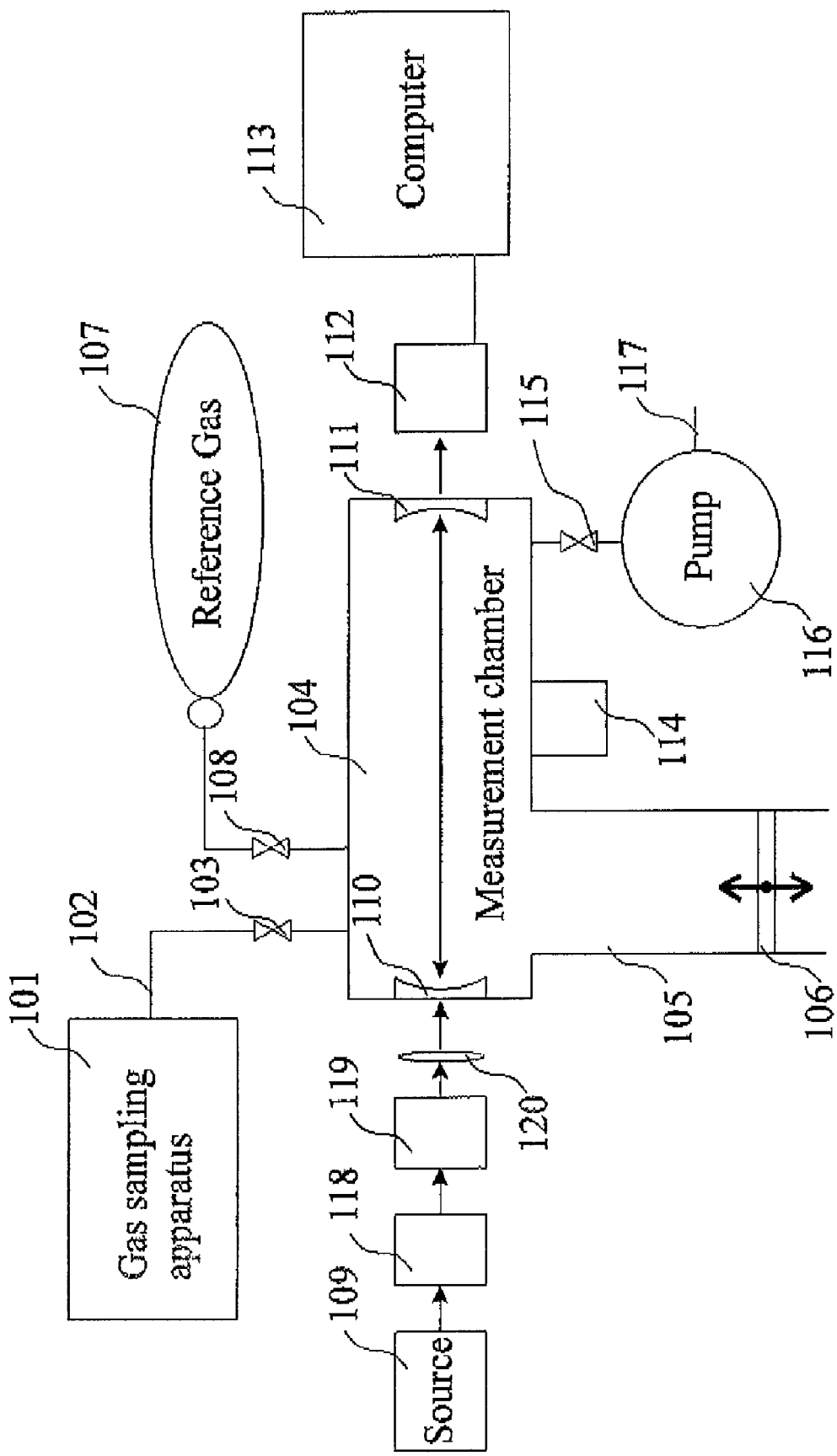
FIG. 1 shows the preferred embodiment of the gas measurement apparatus used for static gas measurements.

As used herein, "analyte" means any substance or chemical constituent that is undergoing analysis.

As used herein, "frequency" means the optical frequency of an electromagnetic wave. It is represented by the symbol "v". It is expressed in the wavenumber units ($cm^{-1}$) usually employed in infrared spectroscopy. Frequency v in $cm^{-1}$ units can be transformed to frequency f in Hertz units by multiplication with the speed of light c, i.e. f=cv where $c \approx 3 \times 10^{10}$ cm $s^{-1}$.)

As used herein, "pulsed", when used to qualify light, refers to a rapid, transient change in the amplitude of light from a baseline value to a higher value, followed by a rapid return to the baseline value, by one or several mechanisms internal or external to the light source. In such a laser pulse system, the amount of time spent in the higher amplitude state is much shorter than the time spent in the baseline state. The laser pulse system may produce a single pulse, or may be engineered to produce regular and periodic pulses. As used herein, "monochromatic", when used to qualify the frequency bandwidth of light, means a bandwidth where the full-width half-maximum frequency spread is less than the free spectral range of the cavity resonance modes, i.e. $\Delta v_{FWHM} < (2\,nL)^{-1}$ where $\Delta v_{FWHM}$ is the full-width half-maximum (FWHM) frequency spread in units of $cm^{-1}$, n is the relative index of refraction of the medium within the cavity, and L is the cavity length in units of cm.

As used herein, "widely-spaced", when used to quality the frequency spacing between the centers of monochromatic light peaks producible by a source, means that the frequency separation between the peaks is at least twice the fill-width half-maximum frequency spread of the peaks, i.e. $\Delta v_{ceners} > 2\Delta v_{FWHM}$.

As used herein, "computer" means any device capable of manipulating data according to a list of instructions.

As used herein "breath" means a vapour that includes both exhaled air from the lungs or perspiration vapour, or sweat vapour transpired through the skin of an animal, including a human.

The development and improvement of cavity ringdown spectroscopy (CRDS) technologies over the last few decades, e.g. U.S. Pat. No. 5,528,040 Lehmann and U.S. Pat. No. 6,865,198 Taubman, has made possible the detection of trace gases to sub-ppbv (parts per billion per volume) sensitivity. By coupling a CRDS cavity with a multiple emission frequency laser, for example a $CO_2$ or CO gas tube laser or a solid-state diode or quantum cascade laser, a multitude of analytes having optical absorption spectra overlapping the laser emission frequencies can be accurately measured. In particular, molecules composed of two or more atoms show highly distinct absorption bands, characteristic of their vibrational and rotational energy levels, in the molecular "fingerprint" frequency region of the infrared spectra between 100 $cm^{-1}$ and 2000 $cm^{-1}$. Thus, hundreds of substances, for example volatile organic compounds (VOCs) which are relevant to medical monitoring and disease diagnosis using exhaled breath or other exhalations e.g. U.S. Pat. No. 7,101,340 Braun, U.S. Pat. No. 6,540,691 Phillips, WO 02/090935 Patel, in addition to a multitudes of compounds of interest in environmental monitoring, explosives detection and industrial process control among others, can be measured by a CRDS apparatus having a plurality of laser emission frequencies within the infrared fingerprint region. In addition, within this fingerprint spectral range, the 800 $cm^{-1}$ to 1200 $cm^{-1}$ interval is especially useful for light absorption measurements since it is relatively transparent to the interfering effects of the major water and $CO_2$ absorption bands.

The ultra-high sensitivity laser-based cavity-enhanced gas detection devices described in the patent and scientific literature typically use current-controlled solid-state quantum cascade or diode laser sources to measure molecular absorption in a ringdown cavity or photoacoustic cell, e.g. U.S. Pat. No. 6,865,198 Taubman, U.S. Pat. No. 5,528,040 Lehmann, U.S. Pat. No. 6,363,722 Berry, WO Pat 02/090935 Patel. As such, these devices are capable of measuring only one or a few specific analytes. This is done by tuning the frequency of the laser source to a fundamental absorption line peak of the pre-determined analyte to quantity. Quantum cascade laser tuning is performed by modifying an electric current sent through the semiconductor element, which changes its temperature by ohmic heating. A change in semiconductor temperature changes its dimensions, thus altering the frequency or frequencies of laser radiation it can emit. Accurate analysis of a mixture using this technique requires that the gaseous sample containing the analytes of interest be present at a reduced pressure in the cavity, in order to minimize pressure-broadening of the analytes' absorption lines which decreases the magnitude of their peaks with respect to the background absorption.

In order to accurately identify and quantify analytes in a complex mixture using laser-based techniques, it is necessary to measure the absorption of the laser lines by the mixture at a multitude of accurately-known and widely-spaced frequencies. Although state-of-the-art solid state laser technologies allow for frequency scanning over limited spectral ranges, it is impractical to know exactly what frequency is being emitted for a given thermal setting without some external frequency measurement device. In contrast, a gas tube laser (e.g. $CO_2$, CO) will emit at a series of quasi-evenly-spaced, well-known frequencies that can be rapidly selected using a rotating diffraction grating apparatus. Gas tube laser technology has a long history and is a stable and robust way of generating infrared radiation at precisely-known frequencies.

The apparatus of the present invention is intended to collect a gas or liquid sample containing at least one analyte to be identified and quantified, wherein a portion of the sample is directed into a measurement chamber which contains highly-reflective mirrors, measure (and optionally regulate) the pressure and temperature of the sample in the measurement chamber, shine a series of mode-matched and frequency-matched light pulses of known distinct frequencies into the ringdown cavity formed by the measurement chamber mirrors, measure the light pulse decay time within the ringdown cavity by using a detector which is responsive to the intensity of light within the measurement chamber, sample and store the signals produced by the detector, calculate the light attenuation due to the sample mixture in the measurement chamber, identify the analytes present in the sample mixture and calculate their concentrations.

FIG. 1 illustrates the preferred embodiment of the apparatus used for static gas measurements. The gas sample to analyze, collected by gas sampling device 101, enters the apparatus through inlet 102. Device 101 uses one of a variety of gas sampling techniques as are well known in the art. To begin a measurement, measurement chamber 104 and optional piston chamber 105 are evacuated using pump 116. Valves 103 and 108 are closed and valve 115 is open during the evacuation. Once a suitable vacuum has been reached inside the measurement chamber, valve 115 is closed and valve 103 opened to allow the sample gas sitting in 101 to enter the measurement chamber by the suction force of the vacuum therein.

In one non-limiting embodiment of the present invention suitable for exhaled breath analysis, device 101 contains a mouth piece, mask, or other breath sampling equipment as is known to the art, a device to preferentially collect breath from selected parts of the lungs or airway, filters to remove and/or reduce the amount of undesired gases, liquids or aerosol particles, and a bag, bladder or any other container into which the breath sample is drawn.

In one non-limiting embodiment of the present invention suitable for ambient air sample analysis, device 101 contains an external flexible hose, with one end that can be positioned to the area where the sample is to be collected while the other end is connected to an area having a lower pressure, thus enabling an air sample to be drawn into the device.

In one non-limiting embodiment, device 101 is a container containing a remotely-collected gas sample.

In one non-limiting embodiment, device 101 is capable of removal from the system altogether so that opening valve 103 allows air sitting outside inlet 102 to enter the measurement chamber 104.

In an alternate embodiment, inlet 102 contains a filter or any device capable of preventing or impeding solid or liquid particles or certain gases from entering measurement chamber 104.

In an alternate embodiment, valve 103 is connected to a device or series of devices capable of measuring the pressure within measurement chamber 104 as well as opening and closing valve 103. This device or series of devices would automatically close valve 103 once a target gas pressure inside the collection chamber has been reached.

In one non-limiting embodiment, thermal regulation device 144 is attached to measurement chamber 104. This device can measure the temperature inside chamber 104, and optionally modify said temperature by using a cooling or heating mechanism. If the temperature measured by 144 differs too much from the temperatures defined in the gas absorption cross-section database, there are three options:

(1) modify the temperature of chamber 104,
(2) adjust the database cross-sections to the measured temperature by using frequency-dependant temperature-correction parameters, or
(3) a combination of (1) and (2).

In one non-limiting embodiment the pressure of the gas mixture inside the collection chamber is adjusted by using piston 106 which is connected to piston chamber 105. If piston 106 is freely-moving and has negligible friction, then it moves until the pressure inside the collection chamber equals the ambient air pressure outside the apparatus.

In an alternate embodiment, piston 106 is a deformable membrane, for example a bag or bellow.

In an alternate embodiment, piston 106 is connected to a driving device used to deliberately change the measurement chamber pressure to a desired value by changing the volume of piston chamber 105 in an appropriate fashion. This capability is useful for optimizing the measurement sensitivity to certain analytes in the mixture, since the shapes of the molecular cross-sections as function of frequency change as function of pressure. It is possible to find optimal pressures that enhance the sensitivity of the device to certain analytes while minimizing unwanted interference effect by others.

In an alternate embodiment, pump 116 is replaced by a fan, ejector or any other device capable of removing gas from a container, or any combination thereof.

Figure 2:
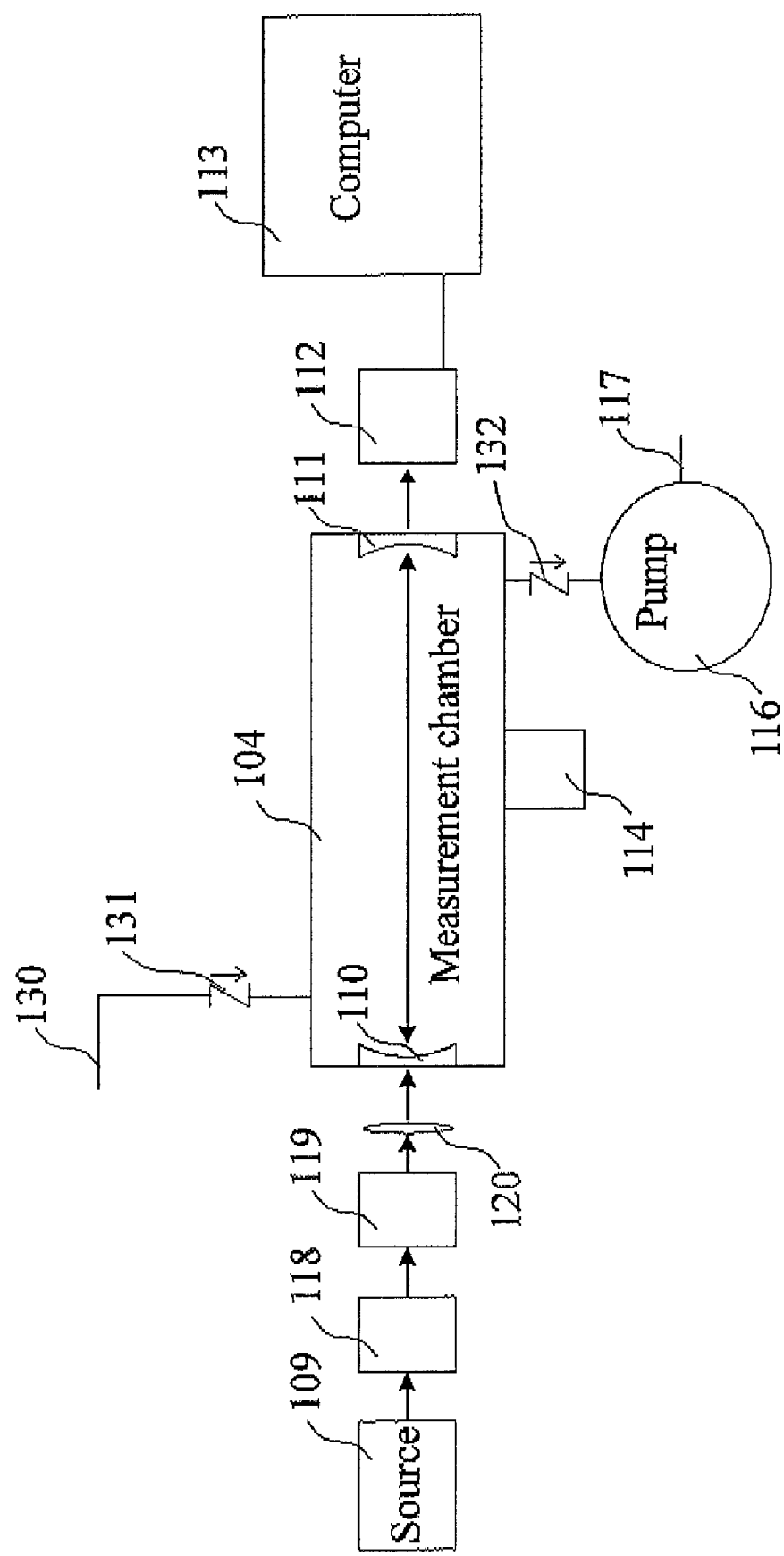
FIG. 2 shows an alternate embodiment of the gas measurement apparatus used for gas flow measurements.

FIG. 2 shows an alternate embodiment of the apparatus used to identify and quantify the components of a continuously flowing gas. In this alternate embodiment, gas inlet 130 is located where a gas sample is to be drawn. The sampled gas flows through the measurement chamber 104 into pump 116, by the pressure differential existing between 130 and 116. The gas removed by pump 116 exits through outlet 117. A temperature measurement/control device 114, as described in the discrete gas sampling embodiment shown in FIG. 1, may also be included.

In an alternate embodiment, inlet 102 contains a filter or any device capable of preventing or impeding solid or liquid particles or certain gases from entering measurement chamber 104.

In an alternate embodiment of the flowing gas measurement apparatus shown in FIG. 2, at least one of flow valve 131 and 132 are included. These valves are check valves or any valve designed to control the direction of the gas flow. They are used to control the direction of the flow in and out of the measurement chamber.

In an alternate embodiment of the flowing gas measurement apparatus shown in FIG. 2, thermal regulation device 114 is attached to measurement chamber 104. This device can measure the temperature inside chamber 104, and optionally modify said temperature by using a cooling or heating mechanism. If the temperature measured by 114 differs too much from the temperatures defined in the gas absorption cross-section database, there are three options:

(1) modify the temperature of chamber 104,
(2) adjust the database cross-sections to the measured temperature by using frequency-dependant temperature-correction parameters, or
(3) a combination of (1) and (2).

In an alternate embodiment, pump 116 is replaced by a fan, ejector or any other device capable of removing gas from a container.

Figure 3:
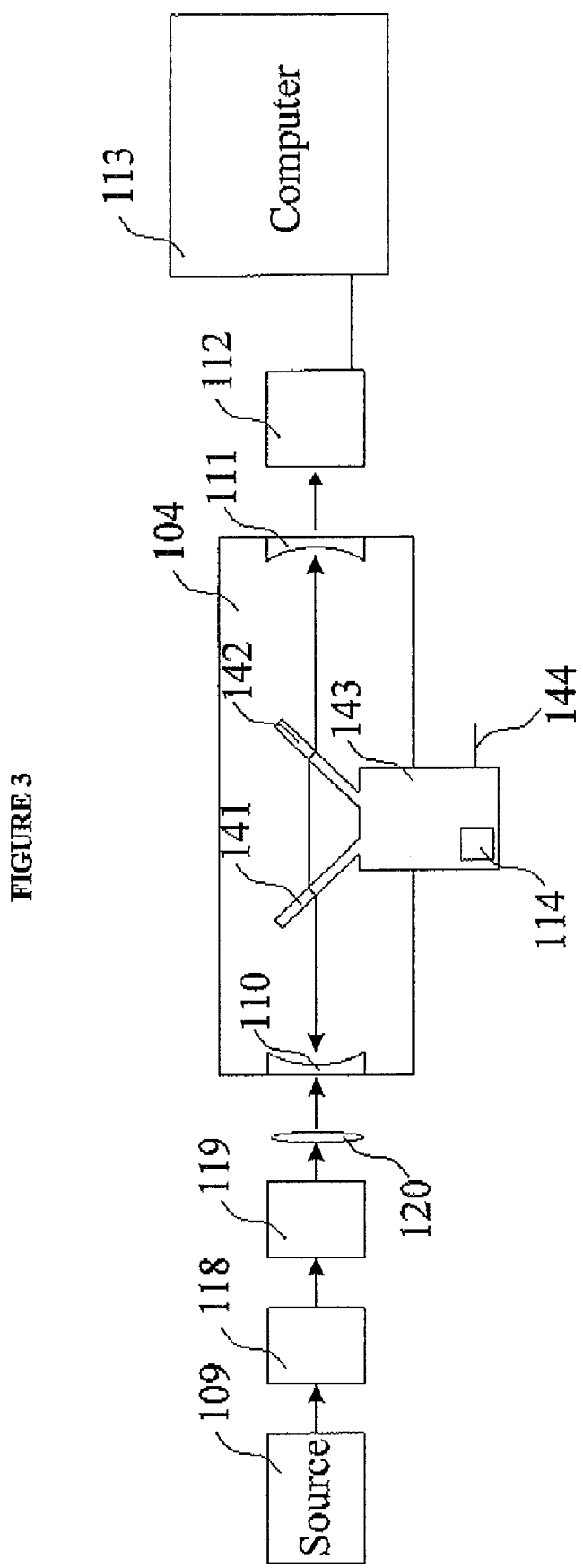
FIG. 3 an alternate embodiment of the measurement apparatus used for liquid absorption measurements.

FIG. 3 shows an alternate embodiment of the apparatus used to identify and quantify the components of a liquid sample. In this embodiment, a complex liquid mixture to analyze is inserted into liquid sample chamber 143 through inlet 144, Chamber 143 is designed in a manner such that the liquid mixture within it can enter two flat chambers 141 and 142. The walls said chambers 141 and 142 are composed of an appropriate transparent substance. The light produced by source 109 which enters the measurement chamber 104 is linearly polarized, either inherently due to the nature of the source or by using a polarizer or polarizing filter, such devices known to those skilled in the art. Thus, by keeping the normals of the surfaces of liquid cavities 141 and 142 tilted to Brewster's angle and appropriately aligning them with respect to the polarization of light within the cavity, it is possible to make the chamber walls of 141 and 142 practically transparent to the light within measurement chamber 104. In addition, having the two chambers oriented in opposite directions cancels out refractive effects within 104, as shown by the segmented double-sided arrow inside 104 in FIG. 3 that illustrates a typical beam path. The inside of measurement chamber 104 is evacuated to ensure that any attenuation of light within it will be largely due to absorption by the liquid inside 141 and 142 and the imperfect reflectivity of measurement chamber mirrors 110 and 111.

In an alternate embodiment of the liquid measurement apparatus shown in FIG. 3, thermal regulation device 114 is attached to measurement chamber 104. This device can measure the temperature inside chamber 104, and optionally modify said temperature by using a cooling or heating mechanism.

Once the sampled mixture inside the measurement chamber 104 is ready to be analyzed, monochromatic light of a known or determinable frequency is produced by source 109. In the preferred embodiment, source 109 is a $CO_2$ laser. This type of laser is particularly useful since the 920 $cm^{-1}$ to 1020 $cm^{-1}$ frequency range where principal-isotope $CO_2$ lasers emit over 50 lines lies within the previously-defined highly-transparent interval of the "fingerprint" region of the infrared spectrum. Single-mode, low-pressure $CO_2$ lasers are highly monochromatic, a feature that facilitates coupling the fundamental optical resonance mode of the ringdown cavity. The rapid selection of a desired emission frequency in a gas laser is performed by using a scanning diffraction grating or any other frequency-determining device. The control of the frequency scanning device is preferably automated in order to synchronize the emitted frequencies to a pre-defined measurement sequence.

In the preferred embodiment, an acousto-optic modulator (AOM) 119 is used to modulate the intensity of the light produced by source 109. In the preferred embodiment, lens system 120 is designed to match $TEM_{00}$ mode light produced by the $CO_2$ laser to the $TEM_{00}$ mode resonance of the ringdown cavity. In the preferred embodiment lens system 120 is a single convex parabolic or spherical lens, with focal length, source-to-lens separation and lens-to-ringdown-cavity separation values selected to optimize $TEM_{00}$ mode-matching between the laser and ringdown cavity.

The ringdown cavity is located inside measurement chamber 104. It is formed by two highly reflective mirrors 110 and 111, whose surface diameters and radii of curvature allow the formation of $TEM_{00}$-mode resonance between the mirrors. In the preferred embodiment, mirrors 110 and 111 are positioned into cutaway areas of the measurement chamber walls, thus allowing light to enter and exit the ringdown cavity. A seal between the mirrors and the measurement chamber prevents the sample mixture from exiting the measurement chamber. In the preferred embodiment, the separation between the mirrors can be finely tuned to at least micron precision by using for example one or several piezo-electric transducers (PZT). Mirror separation is adjusted, preferably by an automated mechanism that may include servo-control, until the main $TEM_{00}$ cavity resonance mode corresponding to the incoming light frequency is excited.

With the cavity mirrors adjusted to maximize resonance with the incoming source fight, a light pulse is sent into the ringdown cavity. During the pulse's high intensity period, a fraction of its light resonates within the cavity. Then, once the pulse transitions to its low intensity period, the light remaining between the cavity mirrors rings down. The rate of decay is measured using the detector 112 which measures the intensity of the small fraction of the cavity light leaking out from the outer surface of mirror 111.

The preferred embodiment of detector 112 for ringdown measurements using a $CO_2$ laser source is a photovoltaic semiconductor such as HgCdTe that produces an electrical current proportional to the number of incoming photons. The time-varying electrical current produced by detector 112 is converted to a proportional voltage that is then measured, digitized and stored by computer 113. During a ringdown event the measured voltage decays exponentially. The decay time $\tau$ is defined as the exponential-folding time of the measured voltage V(t) as function of time, i.e.

$$V(t)=V_0 \exp(-t/\tau)+V_b \quad \{EQ\ 1\}$$

where $V_0$ is the voltage at the beginning of the decay and $V_b$ is a constant background.

The decay time is related to the separation between the cavity mirrors L [cm], the unitless reflectivity R(v) of the cavity mirrors at the laser frequency v, the speed of light c [cm s$^{-1}$], and the frequency-dependent optical density from the unknown mixture to be analyzed k(v) [cm$^{-1}$] and from other background analytes in the measurement chamber $k_{bg}(v)$ [cm$^{-1}$], by the cavity equation $$\tau(v) = \frac{L}{c[(1 - R(v)) + k_{bg}(v)L + k(v)L]}. \quad \{EQ\ 2\}$$

Decay times $\tau$ are obtained for a series of source frequencies in a sequential manner.

In an alternate embodiment of source 109, said source is a $CO_2$ laser containing several different isotopes of $CO_2$, or is a series of $CO_2$ lasers each containing a different isotope and pointed to a device such as a controllable rotating mirror enabling light from a selected laser source to be chosen. The use of multiple isotopes increases the number of monochromatic lines producible by the source and extends its frequency range. For example as taught by the prior art; including a $^{14}C^{18}O_2$ isotope extends the frequency range down to 840 cm$^{-1}$, and including a $^{12}C^{18}O_2$ isotope extends the range up to 1120 cm$^1$, as taught in Status of $CO_2$ Isotope Lasers and Their Applications in Tunable Laser Spectroscopy, Freed, C., *IEEE Journal of Quantum Electronics*, Vol QE-1, No 8, 1982. Using a multiple-isotope source increases measurement sensitivity and the number of detectable analytes.

In an alternate embodiment of source 109, said source is capable of producing pulsed light such that modulator 119 is no longer required and is removed from the apparatus.

In an alternate embodiment of source 109, said source is any other type of broadly tunable laser, for which the optical frequencies can be determined with adequate accuracy through techniques as known in the art.

In an alternate embodiment of lens system 120, said lens system is any combination of one or several lenses and/or mirrors.

In an alternate embodiment of the apparatus of the present invention, automated attenuator 118 is positioned after the source to regulate the intensity of the pulsed light generated for ringdown measurements. In the preferred embodiment of the source 109 where it is a $CO_2$ laser, the light emerging from said source is linearly polarized and so attenuator 118 could be an automated rotating linear polarizer-analyzer.

In an alternate embodiment of the apparatus, a frequency-doubling crystal is inserted somewhere between source 109 and mirror 110 for the purpose of generating additional groups of monochromatic laser frequencies.

Analysis of Absorption

A reference measurement, preferably performed on a periodic basis, is used to eliminate the majority of the parameters in EQ 2 and therefore simplify the problem of extracting k(v) from the measurement of $\tau(v)$. For a reference measurement, the ringdown time constant $\tau^0(v)$ can be described by a slightly altered version of EQ 2, i.e.

$$\tau^0(v) = \frac{L}{c[(1 - R(v)) + k_{bg}(v)L]}, \quad \{EQ\ 3\}$$

where $k_{bg}(v)$ encompasses the total absorption at frequency v from the all analytes present in the reference measurement. It is now possible to obtain a simple expression for the optical density k due to the components in complex mixture that are not present in the reference measurement by combining EQ 2 and EQ 3:

$$k_i = \frac{\tau_i^0 - \tau_i}{c\tau_i^0 \tau_i}, \quad \{EQ\ 4\}$$

where i is an index representing frequency.

Figure 4:
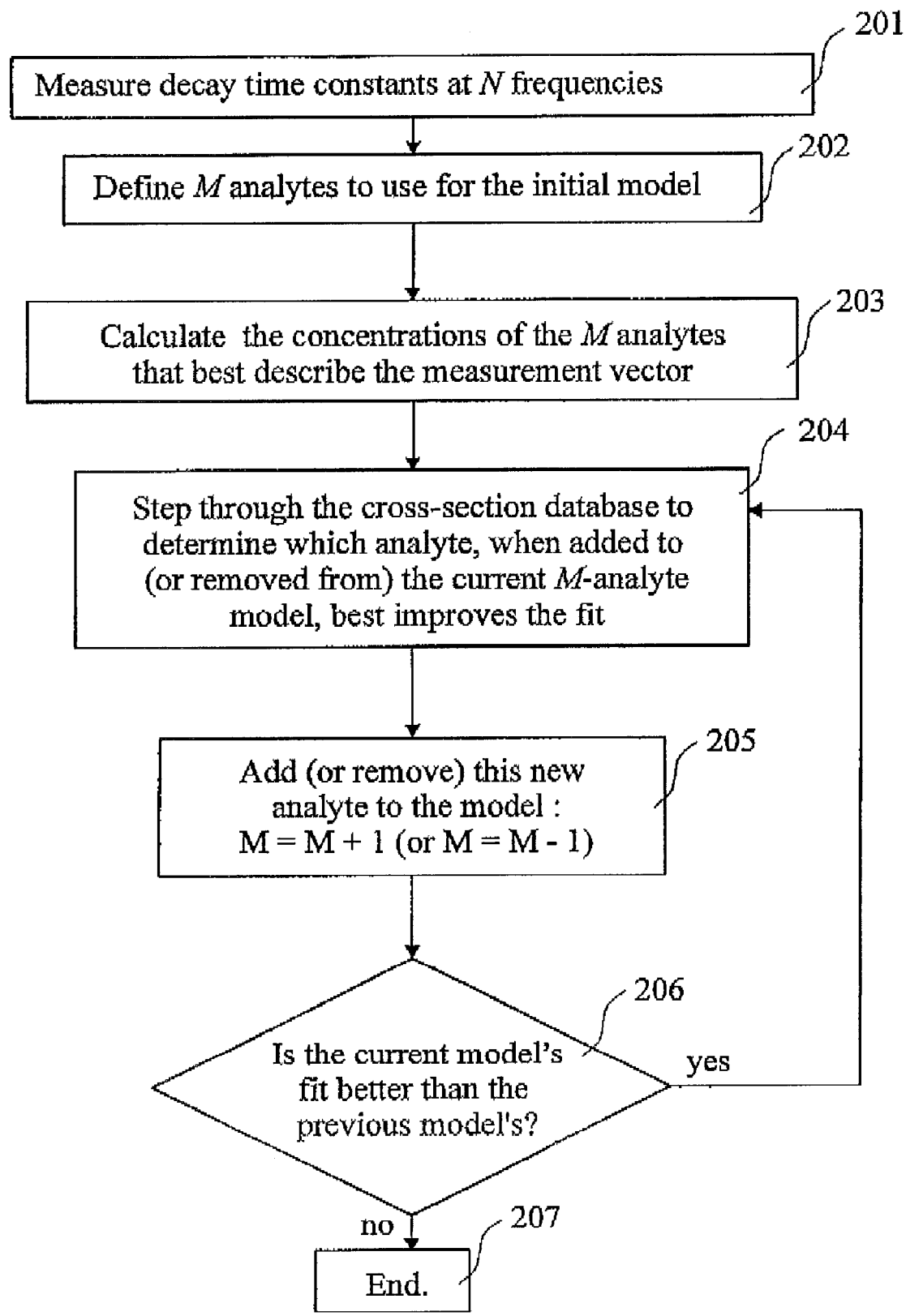
FIG. 4 shows a process diagram of the algorithm used to identity and quantify analytes in a complex mixture using measurements obtained with the apparatus shown in either FIG. 1, FIG. 2 or FIG. 3.

FIG. 4 illustrates the preferred embodiment of the algorithm used for identifying and quantifying the components of a complex mixture of trace gases, using measurements obtained with the apparatus shown in either FIG. 1, FIG. 2 or FIG. 3. Since the source emission frequencies used in the measurements are not tuned to the peak absorption frequencies of any particular analyte, the measurement is not deliberately biased towards said analyte. As such, the apparatus and method is uniquely suited to the purpose of identifying and quantifying the multiple components of an unknown complex mixture in an unbiased manner.

For a gaseous mixture, the absorption features for a given molecule can be measured if the total mixture pressure is sufficiently high, such as 1 atmosphere, even when the absorption peaks of the analytes in the mixture do not directly overlap with the source emission frequencies. This is due to the pressure-broadeening effect that broadens the shapes of the spectral lines as the pressure increases, however without significantly decreasing the total absorption cross-section integrated over a given spectral range. The shapes of molecular absorption spectra are unique for each molecule, and it is possible to model the vector of the total optical density at each laser frequency as a linear superposition of the optical densities of each molecule. Thus, at a given laser frequency represented by the index i, the total optical density $k_i$ [cm$^{-1}$] is the sum of the frequency-dependent molecular absorption cross-sections $\sigma_{ij}$ [cm$^2$ molecule$^{-1}$] multiplied by the molecular concentrations $\rho_j$ [molecule cm$^{-3}$] for each absorbing analyte j, i.e.

$$k_i = \sum_j \sigma_{ij} \rho_j \quad \{EQ\ 6\}$$

The absorption cross-section for a given molecule at a given frequency, $\sigma_{ij}$, is single-valued for given pressure and temperature conditions. Extensive libraries of absorption cross-sections, measured for various temperatures at ambient atmospheric pressure, have been compiled for hundreds of compounds of interest, e.g. the PPNL and NIST databases (Gas Phase Databases for Quantitative Infrared Spectroscopy, Sharpe et. al., *Applied Spectroscopy* Vol 58, No 12, 2004). More detailed pressure and temperature correction parameters have also been measured by several research groups for various molecules, and this data is available in the scientific literature.

The use of absorption cross-sections to model the absorption by a molecule at a given frequency is a simpler and faster approach than the line-by-line modeling methods often used for detailed analysis of gas-phase infrared spectra. At a given temperature and pressure, the absorption cross-section for each absorbing analyte at each laser frequency provides sufficient information to obtain accurate quantification of the analytes of interest. In contrast, if the usual line-by-line technique were used, accurate knowledge of line centers, line strengths and temperature and pressure broadening parameters would be required for all the absorbing analytes in the mixture in order to compute the optical density at the frequency, pressure and temperature of interest. Since line-by-line absorption parameters have only been defined for a handful of small molecules, the use of absorption cross-sections becomes necessary for the analysis of complex mixtures.

As shown in FIG. 4, step 201 of the analysis algorithm consists of the measurement of the ringdown decay titnes at N laser wavelengths for both the reference measurement analytes ($\tau^0_i$ where i=1 to N) and the mixture of trace analytes to be analyzed ($\tau_i$ where i=1 to N). At a given laser frequency, the total optical density $k_i$ due to the analytes in the mixture minus the analytes present in the reference measurement is given by EQ 4. If we assume there are M unknown analytes in the cell, then the absorption at laser line i can be described as the sum of the contributions of each analytes, i.e. EQ 6, A convenient way to express EQ 6 is to replace the absorption cross-section $\sigma_{ij}$, [cm$^2$ molecule$^{-1}$] by $k^0_{ij}$, the reference optical density, i.e.

$$k_{ij}^0 = \sigma_{ij} N_0 \quad \{EQ\ 7\}$$

where $N_0$ is the total number of molecules per cm$^3$ at a given pressure and temperature. The total optical density at a given frequency can therefore be expressed as $$k_\epsilon = \Sigma_{j=1}^M k_{ij}^0 n_j \quad \{EQ\ 8\}$$

where $n_j$ is the fractional analyte concentration: the vector that the algorithm is designed to calculate.

The problem of determining the best-fit $n_j$ can be reduced to the solution of a linear equation y=Kx+ϵ, where y is the measurement vector composed of the elements $$y_i = \frac{\tau_i^0 - \tau_i}{c\tau_i^0 \tau_i}, \quad \{EQ\ 9\}$$

x is the vector of analyte concentrations we wish to fit, i.e. $x_j = n_j$, K is a matrix consisting of the elements $k^0_{ij}$, and ϵ represents the measurement error. The least-squares solution of the linear equation, which provides an estimator of the concentrations of the analytes in the mixture, is.

$$\hat{x} = (K^T S_\epsilon^{-1} K)^{-1} K^T S_\epsilon^{-1} y \quad \{EQ\ 10\}$$

where $S_\epsilon$ is the measurement error covariance. The measurement errors axe assumed to be normally distributed with a variance $\sigma^2_i$ which can be defined for each laser line i. The matrix $S_\epsilon$ is thus composed of the elements $\sigma^2_i$ in the diagonal, with zeros in the off-diagonal elements since we assume individual measurement errors to be uncorrelated.

More sophisticated versions of the least-squares solution equation, which could aid in obtaining more accurate results for $\hat{x}$, could include a priori and probability distribution functions (PDF) of the x vector elements, probabilistic links between the concentrations of various analytes, and uncertainties in the K matrix absorption cross sections. However, these more sophisticated solutions are in principle the same technique, and no limitation in this invention is assumed when using the general model.

Once the ringdown time measurements of step 201 have been obtained and the corresponding measurement vector y has been derived, the iterative process of finding and quantifying the most likely analytes in the measurement chamber can begin. In step 202, a first-guess model consisting of M analytes and their estimated concentrations is defined, and their reference optical densities at each laser frequency are entered in the initial X matrix columns. Then in step 203, the most likely concentrations of each analyte in the M-analyte model are calculated. This could be done for example by using the least-squares solution of the linear equation, shown in EQ 10, to calculate the vector $\hat{x}$ whose elements are the estimated concentrations of each analyte.

In step 204, P new models are generated by iteratively progressing through the database which contains reference optical density parameters for P analytes. If the $P^{th}$ analyte is already part of the M-analyte model, then the $P^{th}$ model is defined as the M-analyte model with the $P^{th}$ analyte removed, i.e. it becomes a M=M−1 analyte model. Otherwise, the $P^{th}$ analyte is added to the M-analyte model and thus the $P^{th}$ model becomes a M=M+1 analyte model. The best-fit concentrations for each analyte in each of the P models is then determined.

In step 205, the model that best fits the measurement vector is retained, and the others are discarded. The goodness-of-fit may be estimated by calculating a fit parameter that incorporates the degrees of freedom (entropy) in the model, which in this case is related to the total number of analytes in the $n_j$ vector. An entropy-based goodness-of-fit metric such as the Akaike Information Criterion (ATC) can be used for this purpose (Akaike, Hirotsugu (1974) "A new look at the statistical model identification". *IEEE Truansactions on Automatic Control* 19 (6): 716-723)). When using an entropy-based fit criterion it is possible that removing an analyte can improve the fit of the model to the measurement, although typically an added analyte improves the fit.

In step 206, if the goodness-of-fit estimator of the new model is better than the goodness-of-fit estimator of the previous iteration of the model, then the algorithm goes to step 204 where another analyte is added to (or removed from) the model to further improve the fit. On the other hand, if the new model does not improve the fit of the model to the measurement vector, then the algorithm ends at step 207 since no further value can be obtained by adding or removing analytes to the model. At this point the best-fit analytes and their concentrations are presented to the user. A check of the residual between the modeled and measured absorption is made at this point. If the residual is larger than the measured instrument noises, or if residual absorption features suggesting the presence of additional analytes that are not in the model are measured, then a second larger database containing qualitative absorption spectra could be queried in order to identify possible additional analytes in the mixture.

EXAMPLE 1

Static Gas Measurement

When using the preferred embodiment of the apparatus shown in FIG. 1, valves 103 and 108 are closed and valve 115 is opened. Measurement chamber 104 is then evacuated using pump 116. In the preferred embodiment, once an appropriately low measurement chamber pressure has been reached, valve 108 is closed and a series of ringdown measurements is then performed in the manner described in Section II. From these measurements, the ringdown time constant $\tau^0(v)$ is obtained for a series of source frequencies in a sequential manner. From the measured reference gas decay time constants and the complex gas mixture decay time constants, the optical densities $k(v)$ can be calculated for a series or source frequencies using EQ 4. Note that for this embodiment) $k_{bg}(v)=0$ in EQ 2 and EQ 3.

In an alternate embodiment of the reference measurement method, the reference measurement is performed by inserting a gas from reference gas cylinder 107 into measurement chamber 104 rather than measuring the ringdown time for an evacuated cavity. This is done to enhance the sensitivity to analytes of interest by removing the contribution from interfering analytes from the optical density measurement. To begin a reference measurement using this embodiment, valves 103 and 108 are closed and valve 115 is opened. Measurement chamber 104 is then evacuated using pump 116. Valve 115 is then closed and valve 108 opened to allow gas to exit from reference gas container 107 and enter measurement chamber 104. The gas inside reference gas container 107 can contain any known mixture of gases. With the pressure and temperature of the reference gas in the measurement chamber measured and regulated in the manner described in Section I, a series of ringdown measurements is then performed in the manner described in Section II. From these measurements, the ringdown time constant $\tau^0(v)$ is obtained for a series of source frequencies in a sequential manner. From the measured reference gas decay time constants and the complex gas mixture decay time constants, the optical densities $k(v)$ can be calculated for a series of source frequencies using EQ 4. Note that for this embodiment, $k_{bg}(v)$ in EQ 2 and EQ 3 represents the combined optical densities from all the gases in the reference cell.

An example of the usefulness of this method in increasing analyte detection sensitivity for exhaled breath measurement follows. In this case, the reference mixture inside cylinder 107 contains a typical mixture of the principal gases included in human breath, i.e. $N_2$, $O_2$, $CO_2$, $H_2O$ and $NH_3$, at typical exhaled-breath concentrations. The infrared-absorbing analytes amongst the former list, i.e. $CO_2$, $H_2O$, $NH_3$, are present at much larger concentrations than the trace gas analytes of interest to medical diagnosis. Indeed, they typically represent over 99% of the total optical density in a typical exhaled breath mixture. By including them in the reference measurement we remove a large portion of their contribution to the measured optical density $k_i$ [cm$^{-1}$]. This enhances the relative contribution of the trace gases to the total signal and reduces the uncertainty in their determined concentration. This can be shown by using a simple 2-gas model consisting of a trace gas of interest having an optical density $k_1$ (i.e. a VOC) and a buffer gas (i.e. $CO_2$) having an optical density $k_2$. A simple error-propagation calculation shows that the relative error in the concentration of trace gas $n_1$ [ppbv] obtained is related to the relative uncertainties in the absorption cross-sections of the two gases, $e_1$ and $e_2$, and the fraction of buffer gas absorption, as, $$\frac{\Delta n_1}{n_1} = -e_2 \frac{1}{1/\alpha - 1} - e_1. \quad \{EQ\ 5\}$$

For example, if $\alpha=0.99$, then the contribution from cross-section uncertainty $e_2$ to the retrieved trace gas concentration is magnified by a factor of nearly 100. Reducing the effective concentration of the buffer gas fraction by half (which requires that the reference cylinder contains 99% of the amount of buffer gas in the mixture to be analyzed), reduces the error contribution to a factor of 1 instead of 100. It should be noted that the above uncertainty calculation is a simplistic model that assumes only one spectral point, but nevertheless shows the usefulness of making a reference measurement with a mixture close in composition to the complex mixture to be quantified.

In an alternate embodiment of the reference measurement method, reference gas cylinder 107 is removed from the apparatus in FIG. 1. In this case, the reference gas is simply ambient air. To begin a reference measurement using this embodiment, valves 103 and 108 are closed and valve 115 is opened. Measurement chamber 104 is then evacuated using pump 116. Valve 115 is then closed and valve 108 opened to allow ambient air outside valve 108 to enter measurement chamber 104 through the suction force due to the pressure gradient between ambient air and the measurement chamber. With the pressure and temperature of the reference gas in the measurement chamber measured and regulated in the manner described in Section I, a series of ringdown measurements is then performed in the manner described in Section II. From these measurements, the ringdown time constant $\tau^0(v)$ is obtained for a series of source frequencies in a sequential manner. From the measured reference gas decay time constants and the complex gas mixture decay time constants, the optical densities $k(v)$ can be calculated for a series or source frequencies using EQ 4. Note that for this embodiment, $k_{bg}(v)$ in EQ 2 and EQ 3 represents the combined optical densities from all the analytes in the collected ambient air sample.

EXAMPLE 2

Flowing Gas Measurement

When using the gas flow measurement embodiment shown in FIG. 2, a reference measurement is a measurement of the gas flow taken at a time when the composition of said flow is known. With a gas of known composition flowing through the measurement chamber, a series of ringdown measurements is performed in the manner described in Section II. From these measurements, the ringdown time constant $\tau^0(v)$ is obtained for a series of source frequencies in a sequential manner. From the measured reference gas decay time constants and the complex gas mixture decay time constants, the optical densities $k(v)$ can be calculated for a series of source frequencies using EQ 4. Note that for this embodiment, $k_{bg}(v)$ in EQ 2 and EQ 3 represents the combined optical densities from all the analytes in the known flowing reference gas.

EXAMPLE 3

Liquid Measurement

When using the liquid measurement embodiment shown in FIG. 3, a reference measurement is taken when there is no liquid inside chambers 141 and 142. The liquid is removed from said chambers by draining container 143 using outlet 144. A series of ringdown measurements is then performed in the manner described in Section II. From these measurements, the ringdown time constant $\tau^0(v)$ is obtained for a series of source frequencies in a sequential manner. From the measured reference decay time constants and the complex gas mixture decay time constants, the optical densities $k(v)$ can be calculated for a series or source frequencies using EQ 4. Note that for this embodiment $k_{bg}(v)=0$ in EQ 2 and EQ 3.

In an alternate embodiment of the reference measurement for liquids, the reference measurement is obtained by measuring the absorption by a liquid of known composition, for example pure water, in chambers 141 and 142. This is achieved by completely draining the complex-mixture liquid from container 143 by using outlet 144, and then refilling said container and chambers with the known-composition reference liquid by using outlet 144. A series of ringdown measurements is then performed in the manner described in Section II. From these measurements, the ringdown time constant $\tau^0(v)$ is obtained for a series of source frequencies in a sequential manner. From the measured reference decay time constants and the complex gas mixture decay time constants, the optical densities $k(v)$ can be calculated for a series of source frequencies using EQ 4. Note that for this embodiment, $k_{bg}(v)$ in EQ 2 and EQ 3 is the optical density due to all the analytes present in the reference liquid.

While particular embodiments of the present invention have been described in the foregoing, it is to be understood that other embodiments are possible within the scope of the invention and are intended to be included herein. It will be clear to any person skilled in the art that modifications of and adjustments to this invention, not shown, are possible without departing from the spirit of the invention as demonstrated through the exemplary embodiments. The invention is therefore to be considered limited solely by the scope of the appended claims.

What is claimed is:

1. An apparatus for identifying and quantifying the presence of least two analytes simultaneously in a liquid or pressure-broadened gas sample comprising:
    an infrared light source for emitting infrared light in a plurality of discrete monochromatic frequencies;
    a pulse generator for pulsing the infrared light;
    a measurement chamber for receiving
        the infrared light, and
        the sample,
    a pressure regulator for regulating pressure within the measurement chamber;
    a detector for detecting and measuring the intensity of light attenuation from the chamber, and producing a signal indicative thereof; and
    a computer, for receiving the signal and programmed to utilize the signal to simultaneously identify and quantify the at least two analytes.

2. The apparatus of claim 1, wherein the light is selected from the group consisting of a gas laser, a solid-state laser or a quantum cascade laser.

3. The apparatus of claim 1 wherein the gas tube laser is a CO or $CO_2$ laser.

4. The apparatus of claim 3 wherein the $CO_2$ laser is an isotopic $CO_2$ laser.

5. The apparatus of claim 1 wherein the light source comprises multiple coupled light sources.

6. The apparatus of claim 1, wherein the plurality of monochromatic frequencies comprises widely-spaced frequencies.

7. The apparatus of claim 1, wherein the pulse generator is internal or external to the light source.

8. The apparatus of claim 1, wherein the pulse generator is for modulating the intensity of the light source.

9. The apparatus of claim 1, wherein the pulse generator is for producing a single or periodic pulses.

10. The apparatus of claim 1, wherein the pulse generator is an acousto-optic modulator.

11. The apparatus of claim 1, wherein the measurement chamber is a cavity-enhanced chamber.

12. The apparatus of claim 11, wherein the cavity-enhanced measurement chamber is a cavity ringdown chamber.

13. The apparatus of claim 12, wherein the pulsed light source is mode-matched to the cavity ringdown chamber.

14. The apparatus of claim 1, wherein the detector comprises a photovoltaic semiconductor.

15. The apparatus of claim 1, wherein the apparatus further comprises sampling equipment for collecting the sample.

16. The apparatus of claim 1, wherein the apparatus further comprises a temperature regulator for regulating the temperature of the measurement chamber.

17. An apparatus for identifying and quantifying the presence of at least two analytes in a liquid or pressure-broadened gas sample comprising:
    a. an isotopic $CO_2$ infrared laser light source for emitting infrared light in a plurality of discrete, widely-spaced monochromatic frequencies;
    b. an acousto-optic modulator for generating pulses of the infrared light,
    c. a cavity ringdown measurement chamber for receiving:
        the infrared light, and
        the sample;
    d. a pressure regulator, for regulating pressure within the measurement chamber;
    e. a temperature regulator, for regulating temperature within the measurement chamber;
    f. a detector, operatively connected to the measurement chamber, for detecting and measuring attenuation of the infrared light from within the chamber, and producing an electronic current proportional thereto; and
    g. a computer, operatively connected to the detector and for receiving the electronic current, and programmed to:
        i. utilize the electronic current to calculate and produce an absorption spectrum of the sample, and
        ii, compare the absorption spectrum to known analyte absorption cross sections to simultaneously identify and quantify the at least two analytes in the sample.

18. A method for identifying and quantifying the presence of at least two analytes simultaneously in a liquid or pressure-broadened gas sample, the method comprising:
    a. providing an infrared light source for emitting infrared light in a plurality of pulsed, discrete monochromatic frequencies,
    b. providing a measurement chamber for receiving the light and the sample, wherein the temperature and pressure within the chamber are regulated,
    c. providing the sample to the measurement chamber,
    d. providing the light to the chamber,
    e. measuring and determining the absorption for the at least two analytes at each monochromatic frequency and producing an absorption spectrum thereof, and
    f. comparing the determined absorption spectrum with known absorptions cross-sections simultaneously to identify and quantify the at least two analytes.

19. The method of claim 18, wherein the light source is selected from the group consisting of a gas laser, a solid-state laser or a quantum cascade laser.

20. The method of claim 19, wherein the gas laser is a CO or $CO_2$ laser.

21. The method of claim 20, wherein the $CO_2$ laser is an isotopic $CO_2$ laser.

22. The method of claim 18, wherein the light source comprises multiple coupled light sources.

23. The method of claim 18, wherein the plurality of monochromatic frequencies comprises widely-spaced frequencies.

24. The method of claim 18, wherein the infrared light is emitted in a single pulse or periodic pulses.

25. The method of claim 18, wherein the measurement chamber is a cavity-enhanced chamber.

26. The method of claim 25, wherein the cavity-enhanced measurement chamber is a cavity ringdown chamber.

27. The method of claim 26, wherein the pulsed light source is mode-matched to the cavity ringdown chamber.

* * * * *

UNITED STATES PATENT AND TRADEMARK OFFICE
CERTIFICATE OF CORRECTION

| | | |
|---|---|---|
| PATENT NO. | : 8,288,727 B2 | Page 1 of 1 |
| APPLICATION NO. | : 12/517036 | |
| DATED | : October 16, 2012 | |
| INVENTOR(S) | : John Cormier and Denis Dufour | |

It is certified that error appears in the above-identified patent and that said Letters Patent is hereby corrected as shown below:

In the Claims

Column 15, line 24, Claim 1, after "of", insert --at--.

Column 15, line 44, Claim 3, delete "tube".

Signed and Sealed this
Sixteenth Day of September, 2014

Michelle K. Lee
*Deputy Director of the United States Patent and Trademark Office*